United States Patent [19]
Bowey et al.

[11] Patent Number: 5,595,957
[45] Date of Patent: Jan. 21, 1997

[54] TURF AND SOIL DROUGHT STRESS TREATMENT COMPRISING A SILOXANE AND A POLYALKALENE OXIDE SURFACTANT

[75] Inventors: Kenneth G. Bowey, Leders; Neil A. Baldwin, Wilsden, both of England

[73] Assignee: Service Chemicals plc, Northants, England

[21] Appl. No.: 392,495

[22] Filed: Feb. 23, 1995

[51] Int. Cl.$^6$ .............................. A01N 55/10; C09K 17/38
[52] U.S. Cl. .............................. 504/118; 504/193; 71/903
[58] Field of Search .............................. 504/193, 118; 71/903

[56] References Cited

U.S. PATENT DOCUMENTS 5,104,647  4/1992  Policello ................................. 514/772
5,459,121  10/1995  Shin et al. ............................. 504/114

*Primary Examiner*—S. Mark Clardy
*Attorney, Agent, or Firm*—Wood, Phillips, VanSanten, Clark & Mortimer

[57] ABSTRACT

Turf or soil is treated to alleviate drought stress and soil capping and to improve soil water conservation by applying directly to the turf or soil a composition comprising an organosilicone and a polyalkylene oxide surfactant.

17 Claims, No Drawings

TURF AND SOIL DROUGHT STRESS TREATMENT COMPRISING A SILOXANE AND A POLYALKALENE OXIDE SURFACTANT

This invention relates to a method of treating turf and soil to alleviate drought stress and soil capping and to improve water conservation in soil.

In dry periods, turf can be affected by drought stress. This can manifest itself in a number of ways, and in extreme cases the turf may die. Turfgrass maintained on light soil, e.g. sand rootzone golf greens and links golf courses, is particularly prone to drought stress as is turf which is grown in generally poor soil conditions. Curiously, drought stress not only occurs in dry conditions, but also in relatively wet seasons due, for example, to rootbreaks, buried materials close to the surface, or through general inefficiency of an irrigation system. Soils can also suffer drought stress. Thus, on heavy soils, one of the first signs of drought stress is that surface cracks appear on the soil. It will be appreciated that drought stress, in all its various forms, is undesirable and that it would be advantageous to avoid or reduce it.

So-called soil "capping", i.e. crusting of the soil surface, can occur due to the pounding action of raindrops on soil. Capping can give rise to various problems, especially in seedbeds on light soils where it can prevent or reduce seedling emergence, thus resulting in a patchy, uneven sward. It would be desirable to be able to avoid soil capping, or at least reduce its effects.

In many places, water is becoming an ever decreasing resource, as is evidenced by dry rivers, low water tables and frequent restrictions on water usage. Further, in times of water shortage, it is often amenity users of water (e.g. golf courses etc.) where restrictions are enforced. It would, therefore be highly advantageous to be able to treat turf and soil so as generally to improve their water conservation so as to promote efficient use and minimise wastage.

We have investigated these various problems of drought stress, soil capping and water conservation, and we have found a way of treating turf and/or soil whereby these problems can be reduced or overcome.

According to the present invention, there is provided a method of treating turf or soil to alleviate drought stress and soil capping and to improve soil water conservation, which comprises applying directly to the turf or soil an aqueous solution of a composition consisting essentially of a) from 1 to 99% by weight of an organosilicone compound of the general formula $$MD_yD'_xM$$

where
M is $(CH_3)_3SiO_{1/2}$,
D is $(CH_3)_2SiO$ and D' is $CH_3RSiO$,
where
$R=(CH_2)_nO(C_2H_4O)_a(C_3H_6O)_bR_1$,
$R_1$ is H, an alkyl group having 1 to 4 carbon atoms, an alkyl ester group wherein the alkyl group of the ester has 1 to 4 carbon atoms:
n is from 2 to 4;
a is from 3 to 25;
b is from 0 to 25;
wherein
Y is from 0 to 5;
and
X is from 1 to 5: and b) from 99 to 1% by weight of at least one surfactant selected from polyalkylene oxide compounds with the general formula $$R_2-O-(C_2H_4O)_c(C_3H_6O)_dR_3$$

where
c is 0 to 300,
d is 0 to 300, and
$R_3$ is H, or an alkyl group with 1 to 4 carbon atoms; wherein the polyalkylene oxide has a molecular weight in the range 300 to 15000; and a second different surfactant.

Some of the compositions which are used in accordance with the present invention are described in U.S. Pat. No. 5,104,647. This patent describes a surfactant blend comprising 1 to 99 weight percent of an organosilicone surfactant and 1 to 99% weight percent of a polyalkyleneoxide copolymer, wherein (i) the organosilicone surfactant is of the general formula:

$$MD'_xM \quad (I)$$

wherein:
M is $Me_3SiO_{1/2}$
D' is MeRSiO,
Me is $CH_3$
R is $C_nH_{2n}O(C_2H_4O)_a(C_3H_6O)_bR'$
n is from 2 to 4,
a is 3 to 25,
b is from 0 to 25,
R' is hydrogen, an alkyl group having 1 to 4 carbon atoms, or an alkyl ester group wherein the alkyl group of the ester has 1 to 4 carbon atoms.
x is 1 to 5; and (ii) the polyalkyleneoxide copolymer is of the general formula:

$$R''O-(C_2H_4O)_c(C_3H_6O)_d-R'' \quad (II)$$

wherein:
c is 0 to 300,
d is 1 to 300, and
R" is hydrogen or an alkyl group having 1 to 4 carbon atoms: and wherein the organosilicone surfactant is soluble in the polyalkyleneoxide copolymer.

The above U.S. Pat. No. 5,104,647 describes the surfactant blends as useful as pesticide adjuvants. Thus, they are mixed with pesticides (or other active materials) and then the mixture is applied to plants and crops as desired. The surfactant blend serves to increase the dispersing, wetting and spreading of the pesticides. The spreading characteristics are particularly important.

In contrast to the teaching of U.S. Pat. No. 5,104,647, the surfactant compositions of the present invention are not used as adjuvants. Thus, they are not mixed with active materials to assist in the dispersing, wetting and spreading of actives such as pesticides. Instead, they are applied as they are directly on to turf or soil. We have found that, very surprisingly, this results in the treated turf being less prone to drought stress, and the treated soil being less prone to soil capping. Furthermore, and very importantly, the treated soil (as such or below the treated turf) retains its moisture content better than untreated soil, and thus there is an improvement in water conservation.

Whilst some of the compositions used in the present invention are described for use as adjuvants in U.S. Pat. No. 5,104,647, other compositions of the present invention are novel per se and form an aspect of the invention.

Thus, the invention provides a composition for treating turf or soil to alleviate drought stress and soil capping and to improve soil water conservation, which composition consists essentially of an aqueous solution of:

a) from 1 to 99% by weight of an organosilicone compound of the general formula $$MD_yD'_xM$$

where
M is $(CH_3)_3SiO_{1/2}$.
D is $(CH_3)_2SiO$ and D' is $CH_3RSiO$,
where
$R=(CH_2)_nO(C_2H_4O)_a(C_3H_6O)_bR_1$,
$R_1$ is H, an alkyl group having 1 to 4 carbon atoms, an alkyl ester group wherein the alkyl group of the ester has 1 to 4 carbon atoms;
n is from 2 to 4;
a is from 3 to 25;
b is from 0 to 25;
wherein
Y is from 0 to 5; and
X is from 1 to 5; and
b) from 99 to 1% by weight of a second surfactant of the formula $$R_4O(CH_2CH_2O)_nR_5$$

where
n is 1 to 50;
$R_4$ is an alkyl group of up to 20 carbon atoms, or an aryl group optionally having an alkyl substituent with up to 20 carbon atoms;
$R_5$ is selected from hydrogen and alkyl groups having from 1 to 4 carbon atoms.

The invention also provides a composition for treating turf or soil to alleviate drought stress and soil capping and to improve soil water conservation, which composition consists essentially of an aqueous solution of:
a) from 1 to 99% by weight of an organosilicone compound of the general formula $$MD_yD'_xM$$

where
M is $(CH_3)_3SiO_{1/2}$,
D is $(CH_3)_2SiO$ and D' is $CH_3RSiO$,
where
$R=(CH_2)_nO(C_2H_4O)_a(C_3H_6O)_bR_1$,
$R_1$ is H, an alkyl group having 1 to 4 carbon atoms, an alkyl ester group wherein the alkyl group of the ester has 1 to 4 carbon atoms;
n is from 2 to 4;
a is from 3 to 25;
b is from 0 to 25;
wherein
Y is from 0 to 5; and
X is from 1 to 5; and
b) a second surfactant of the formula $$R_4O(CH_2CH_2O)_nR_5$$

where
n is 1 to 50;
$R_4$ is an alkyl group having up to 20 carbon atoms, or an aryl group optionally having an alkyl substituent with up to 20 carbon atoms;
$R_5$ is selected from hydrogen and alkyl groups having from 1 to 4 carbon atoms.
c) a polyalkylene oxide surfactant of general formula $$R_2-O-(C_2H_4O)_c(C_3H_6O)_dR_3$$

where c is 0 to 300; d is 0 to 300; $R_3$ is selected from H and alkyl groups with 1 to 4 carbon atoms; the polyalkylene oxide having a molecular weight of 300 to 15000; wherein the total amount by weight of (b) and (c) is from 99% to 1%.

Preferred second surfactants in the compositions used in the invention are of the general formulae

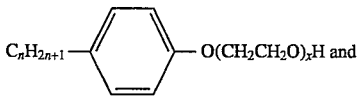

$$C_nH_{2n+1}O(CH_2CH_2O)_xH$$

Of these preferred second surfactants, alkylarylethoxylates are especially preferred, of which the nonyl phenol ethoxylate of formula

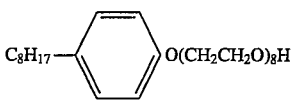

is an example. Another preferred compound has the formula $$C_{12}H_{25}O(CH_2CH_2O)_7H$$

These second surfactants actually prevent spreading of the compositions, and U.S. Pat. No. 5,104,647 teaches against their use for its quite different purposes.

In the method of the invention, the composition of surfactants will preferably be essentially free from other actives. The composition may consist only of the components (a), (b) and (c) if present, dissolved in water.

Various polyalkyleneoxide copolymers are described in U.S. Pat. No. 5,104,647 such as Pluronics (trademark)., Ucon (trademark) and Poly-Tergents (trademark) and these can be used in the present invention. Thus, for example, Pluronic PE 6200 can be used, which has the formula $$HO(CH_2CH_2O)_x(CH_2CH_2CH_2O)_y(CH_2CH_2O)_zH$$

and an average molecular weight of approximately 2500 and an ethylene oxide content of 20% w/w.

The polyalkylene oxide component used in the present invention preferably has a molecular weight of from 300 to 3000. In the formula given above for the polyalkylene oxide, c is preferably from 4 to 15, and (independently of c) d is preferably from 2 to 10. Preferably, the polyalkylene oxide is a polypropylene glycol polymer, for example PPG 400, PPG 1200, PPG 2000 or PPG 4000, which have the formula:

$$HO(CH_2CH(CH_3)O)_xH$$

In the organosilicone component, n is preferably 3, and (independently of n) a is preferably from 3 to 15. The value of b is preferably from 0 to 15.

The organosilicones which can be used in the present invention are those described in U.S. Pat. No. 5,104,647, the teachings of which are incorporated herein by reference.

Among the preferred organosilicones for use in the invention are those in the following Table:

| | TYPE | RATIO EO/PO | END CAP | Molecular Weight |
|---|---|---|---|---|
| Silwet L77 | AP | All E/O | Me | 600 |
| Silwet L720 | AEB | 50/50 | Bu | 12,000 |
| Silwet L722 | AEB | All P/O | Bu | 3,000 |
| Silwet L7001 | AP | 40/60 | Me | 20,000 |

-continued

| | TYPE | RATIO EO/PO | END CAP | Molecular Weight |
|---|---|---|---|---|
| Silwet L7002 | AP | 50/50 | Bu | 8,000 |
| Silwet L7200 | AP | 75/25 | H | 19,000 |
| Silwet L7210 | AP | 20/80 | H | 13,000 |
| Silwet L7230 | AP | 40/60 | H | 29,000 |
| Silwet L7500 | AP | All P/O | Bu | 3,000 |
| Silwet L7600 | AP | All E/O | Me | 4,000 |
| Silwet L7602 | AP | All E/O | Me | 3,000 |
| Silwet L7604 | AP | All E/O | H | 4,000 |
| Silwet L7605 | AP | All E/O | Me | 6,000 |
| Silwet L7607 | AP | All E/O | Me | 1,000 |
| Silwet L7622 | AP | All E/O | Me | 10,000 |
| Silwet 408 | AP | All E/O | H | ~600 |

In the above Table,

AP=Alkyl pendant (non hydrolyzable)

AEB=Alkoxy Endblocked (hydrolyzable)

Me=Methyl

Bu=Butyl

H=Hydrogen

E/O=Ethylene Oxide

P/O=Propylene Oxide

Of the above, the most preferred are Silwet L77 and Silwet 408. We also prefer Silgard 309, Tergopren 5840 and Tergopren 5878 (from Goldschmidt) which are also very close in structure and molecular weight to Silwet L77 and Silwet 408 but whose precise structure and molecular weight are unpublished. Silwet L77 has the structure:

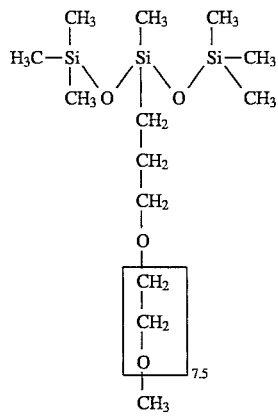

wherein $y=0$, $x=1$, $n=3$, $a=7.5$ and $b=0$ with $R_1$ being a methyl group. This material is available in the market place. Silwet 408 is an uncapped organosilicone, i.e. an organosilicone without a methyl group at the end of the ethylene oxide chain.

Among the polyalkylene oxide surfactants which can be used in the present invention are the following:

Polyalkylene Oxide Surfactants from BASF:

| SURFACTANT | AVERAGE MOLECULAR WEIGHT | WEIGHT % ETHYLENE OXIDE |
|---|---|---|
| Pluronic PE3100 | 1100 | 10% |
| Pluronic PE4300 | 1700 | 30% |
| Pluronic PE6100 | 2000 | 10% |
| Pluronic PE6200 | 2500 | 20% |
| Pluronic PE6400 | 3000 | 40% |
| Pluronic PE6800 | 8500 | 80% |
| Pluronic PE8100 | 2600 | 10% |
| Pluronic PE9200 | 3650 | 20% |

Products from ICI:

| SURFACTANT | AVERAGE MOLECULAR WEIGHT |
|---|---|
| Synperonic L35 | 1900 |
| Synperonic F38 | 5000 |
| Synperonic L42 | 1630 |
| Synperonic L44 | 2200 |
| Synperonic L61 | 2000 |
| Synperonic L62 | 2500 |
| Synperonic L62LF | 2450 |
| Synperonic L64 | 2900 |
| Synperonic L68 | 8350 |
| Synperonic P75 | 4150 |
| Synperonic L81 | 2750 |
| Synperonic P85 | 4600 |
| Synperonic F87 | 7700 |
| Synperonic F88 | 10800 |
| Synperonic L92 | 3650 |
| Synperonic P94 | 4600 |
| Synperonic L101 | 3800 |
| Synperonic P103 | 4950 |
| Synperonic F108 | 1400 |
| Synperonic L121 | 4400 |
| Synperonic F127 | 12500 |

Other block polymers include those produced by the liquid condensation of propylene oxide on an ethylene oxide base e.g.:

| SURFACTANT | AVERAGE MOLECULAR WEIGHT |
|---|---|
| Synperonic PE/25R2 | 3200 |
| Synperonic L31 | 1100 |
| Synperonic L43 | 1850 |
| Synperonic L63 | 2650 |
| Synperonic P65 | 3400 |
| Synperonic L72 | 2750 |
| Synperonic F77 | 6600 |
| Synperonic P84 | 4200 |
| Synperonic F98 | 13500 |
| Synperonic P104 | 5850 |
| Synperonic P105 | 6500 |
| Synperonic L122 | 5000 |
| Synperonic P123 | 5750 |

Other polyalkylene oxide surfactants include:

| SURFACTANT | AVERAGE MOLECULAR WEIGHT |
|---|---|
| Polyglycol P2000E | 2000 |
| Polyglycol P400E | 400 |
| Polyglycol P1200E | 1200 |
| Hodag PPG150 | 150 |
| Hodag PPG400 | 400 |
| Hodag PPG1200 | 1200 |
| Hodag PPG2000 | 2000 |
| Hodag PPG4000 | 4000 |
| Voranol P1010 | 1010 |

Other manufacturers have products similar to these which are known to those skilled in the art of surface chemistry.

Among the second surfactants which can be used in the present invention are the following alkyl phenol ethoxylates:

(a) Those manufactured by Atcros formerly Lankro Chemicals include:

| | HYDROPHOBE | NO. OF MOLES OF ETHYLENE OXIDE |
|---|---|---|
| Ethylan NP1 | Nonylphenol | 1 |
| Ethylan 44 | Nonylphenol | 4 |
| Ethylan 55 | Nonylphenol | 5.5 |
| Ethylan 77 | Nonylphenol | 6.5 |
| Ethylan TU | Nonylphenol | 8 |
| Ethylan BCP | Nonylphenol | 9 |
| Ethylan KEO | Nonylphenol | 9.5 |
| Ethylan DP | Nonylphenol | 12 |
| Ethylan BV | Nonylphenol | 14 |
| Ethylan 20 | Nonylphenol | 20 |
| Ethylan N30 | Nonylphenol | 30 |
| Ethylan HA | Nonylphenol | 35 |

(b) Linear alcohol ethoxylates:

| | HYDROBE | No of Mols of Ethylene Oxide |
|---|---|---|
| Synperonic A2 | $C_{13-15}$ alcohol | 2 |
| Synperonic A3 | $C_{13-15}$ alcohol | 3 |
| Synperonic A4 | $C_{13-15}$ alcohol | 4 |
| Synperonic A6 | $C_{13-15}$ alcohol | 6 |
| Synperonic A7 | $C_{13-15}$ alcohol | 7 |
| Synperonic A9 | $C_{13-15}$ alcohol | 9 |
| Synperonic A11 | $C_{13-15}$ alcohol | 11 |
| Synperonic A14 | $C_{13-15}$ alcohol | 14 |
| Synperonic A20 | $C_{13-15}$ alcohol | 20 |
| Synperonic A50 | $C_{13-15}$ alcohol | 50 |
| Synperonic 91/2.5 | $C_{9-11}$ alcohol | 2.5 |
| Synperonic 91/5 | $C_{9-11}$ alcohol | 5 |
| Synperonic 91/6 | $C_{9-11}$ alcohol | 6 |
| Synperonic 91/8 | $C_{9-11}$ alcohol | 8 |
| Synperonic 91/10 | $C_{9-11}$ alcohol | 10 |
| Dobanol 25-3 | $C_{12-15}$ alcohol | 3 |
| Dobanol 25-7 | $C_{12-15}$ alcohol | 7 |
| Dobanol 25-9 | $C_{12-15}$ alcohol | 9 |

In order that the invention may be more fully understood, the following Examples and tests are given by way of illustration only.

A series of laboratory tests and field trials were carried out on a range of materials in accordance with the present invention, as well as a control of pure water, and a comparative example of a commercially known material. These tests included assessment of the ability to dissolve in cold water, stay in solution and not produce excessive foam. Materials were also tested for phytotoxic effects.

Laboratory based water conservation tests, were carried out, as well as trials on two field sites. The data from these tests are included in Table 1, with the samples tested being as follows:

| Sample No. | Formulation |
|---|---|
| 1 | Control - water |
| 2 | Silwet L77 and Pluronic PE6200 |
| 3 | and PPG 4000 |
| 4 | and nonyl phenol ethoxylate |
| 5 | and PPG 400 |
| 6 | and PPG 1200 |
| 7 | Uncapped Siloxane TP408 and PPG 400 |
| 8 | Silwet L77 and PPG 1200 and nonyl phenol ethoxylate |

-continued

| Sample No. | Formulation |
|---|---|
| 9 | Silwet L77 and PPG 1200 and nonyl phenol ethoxylate |

Pluronic PE6200 is as defined previously herein.

Siloxane TP408 is the same as Silwet L77 (previously defined herein) except that it is uncapped, i.e. the terminal methyl group of the polyalkylene oxide chain is replaced by hydrogen.

PPG 4000 is polypropylene glycol of formula $HO(CH_2CH(CH_3)O)_xH$ of molecular weight 4000.

PPG 400 is polypropylene glycol of formula $HO(CH_2CH(CH_3)O)_xH$ of molecular weight 400.

PPG 1200 is polypropylene glycol of formula $HO(CH_2CH(CH_3)O)_xH$ of molecular weight 1200.

In the laboratory, test conditions resembling those of a semi-arid climate were created using, a "light frame". This consisted of a metal box frame measuring 2 m ×1 m×1 m on top of which were suspended 6 fluorescent light tubes. The apparatus was bench mounted and the lights connected to a timer set at 16 hr illumination, 8 hr darkness daily. A max-min thermometer recorded a daily day-time maximum of 35° C. and night minimum of 16° C.

Using a golf green hole cutter, turf cores were taken to a depth of 6 cm and the soil surface of each core was sealed using a plastic bag and rubber band, so that only the turfgrass surface was exposed. Each core (10 replicates per treatment) was watered with the material under test at equivalent field rates of 5 ml/m² turf area. Each core was weighed daily to determine moisture loss over time. The results are presented as % moisture loss compared to the control (water) loss in Table 1.

The material under test was applied at normal and double application rates (1 ml and 2 ml/m² respectively) in a spray volume of 100 ml/m² water, left unwatered to dry on the turf surface, and checked to see if there were any signs of burning or scorching, or other phytotoxic effects. These tests were done both in the laboratory and the field test work.

The field tests were carried out at Royal Liverpool GC and Ganton GC, where areas of unirrigated fairway were chosen and for each material under test 2×5 m²plots were marked out. The materials were applied at an application rate of 5 ml/m² in 500 ml water using a watering can with dribble bar attachment. Grass vigour in each plot was assessed by an area quadrat method where the % ground cover of healthy grass was recorded.

TABLE 1

| Sample | Dissolves Cold Water | Stays in Solution 5 mins. | Excessive Foaming | Phytotoxic | Laboratory Water Conservations Days After Treatment | | | Field Trials Ground Cover Months After Treatment | | | | Soil Moisture % |
|---|---|---|---|---|---|---|---|---|---|---|---|---|
| | | | | | 3 | 5 | 10 | 1 | 2 | 3 | 4 | |
| 1 | — | — | — | — | 100 | 100 | 100 | 22 | 42 | 39 | 64 | 8.6 |
| | | | | | | | | 49 | 55 | 44 | 60 | |
| 2 | No | Yes | Yes | No | 93.5 | 76.5 | 98.4 | 65 | 59 | 49 | 58 | |
| 3 | No | With Agitation | No | No | 93.8 | 77.0 | 98.2 | 60 | 61 | 60 | 62 | |
| 4 | Yes | Yes | No | Slight | 92.8 | 83.7 | 97.9 | — | — | — | — | 9.0 |
| | | | | | | | | 62 | 65 | 65 | 64 | |
| 5 | Yes | Yes | Yes | No | 89.8 | 82.6 | 97.1 | 79 | 82 | 72 | 79 | |
| 6 | Yes | With Agitation | Yes | No | 90.2 | 77.4 | 96.8 | 69 | 68 | 67 | 52 | |
| 7 | Yes | Yes | No | No | 91.2 | 76.5 | 96.9 | — | — | — | — | 8.8 |
| | | | | | | | | 67 | 70 | 70 | 70 | |
| 8 | Yes | Yes | No | Slight | 91.9 | 78.2 | 95.2 | 84 | 85 | 87 | 74 | |
| 9 | Yes | Yes | No | No | 88.2 | 75.2 | 98.4 | — | — | — | — | 10.4 |
| | | | | | | | | 85 | 87 | 82 | 76 | |

We claim:

1. A method of treating turf or soil to alleviate drought stress and soil capping and to improve soil water conservation, which comprises applying directly to the turf or soil an aqueous solution of a composition consisting essentially of a) from 1 to 99% by weight of an organosilicone compound of the general formula $$M_d y D x' M'$$

where M is $(CH_3)_3SiO$ and M' is $Si(CH_3)_3$
D is $(CH_3)_2SiO$ and D' is $(CH_3)(R)SiO$
where $R=(CH_2)_n O(C_2H_4O)a(C_3H_6O)_b R_1$, $R_1$ is H, an alkyl group having 1 to 4 carbon atoms, an alkyl ester group wherein the alkyl group of the ester has 1 to 4 carbon atoms:

n is from 2 to 4;
a is from 3 to 25;
b is from 0 to 25;
wherein Y is from 0 to 5; and
X is from 1 to 5; and b) from 99 to 1% by weight of at least one surfactant selected from polyalkylene oxide compounds with the general formula $$R_3-O-(C_2H_4O)c(C_3H_6O)_d R_3$$

where
c is 0 to 300;
d is 0 to 300, and
$R_3$ is H, or an alkyl group with 1 to 4 carbon atoms;
wherein the polyalkylene oxide has a molecular weight in the range of 300 to 1500; and c) a second optional different surfactant.

2. A method according to claim 1, wherein the composition consists only of the components (a) and (b).

3. A method according to claim 1, wherein the second surfactant comprises a compound of the general formula $$R_4O(CH_2CH_2O)_n R_5$$

where n is from 1 to 50; $R_4$ is an alkyl group or an aryl group optionally having an alkyl group substituent, the alkyl group having up to 20 carbon atoms;

$R_5$ is selected from H and alkyl groups having from 1 to 4 carbon atoms.

4. A method according to claim 3, wherein in the second surfactant n is from 4 to 20.

5. A method according to claim 3, wherein the second surfactant is an alkylaryl ethoxylate.

6. A method according to claim 3, wherein the second surfactant is nonyl phenol ethoxylate of structure

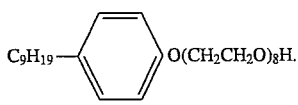

7. A method according to claim 3 wherein the second surfactant is octylphenolethoxylate of structure

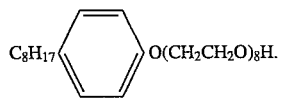

8. A method according to claim 3, wherein the second surfactant comprises a compound of the general formula $$R_4O(CH_2CH_2O)_n H,$$

where n is from 1 to 50 and $R_4$ is an alkyl group having up to 20 carbon atoms.

9. A method according to claim 1, wherein the organosilicone is of the following structure

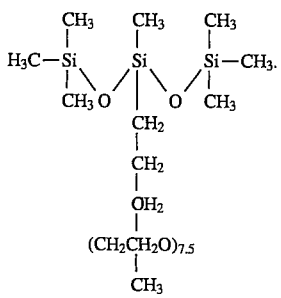

10. A method according to claim 1, wherein the polyalkylene oxide has a molecular weight of from 300 to 3000.

11. A method according to claim 1, wherein in the polyalkylene oxide, c is from 4 to 15, and d is from 2 to 10.

12. A method according to claim 1, wherein the polyalkylene oxide is polypropylene glycol polymer.

13. A method according to claim 1, wherein in the organosilicone, n is 3, a is from 3 to 15 and b is from 0 to 15.

14. A method of treating turf or soil to alleviate drought stress and soil capping and to improve soil water conservation, which comprises applying directly to the turf or soil a composition consisting essentially of an aqueous solution of:

a) from 1 to 99% by weight of an organosilicone compound of the general formula $$MD_yD_x'M'$$

where M is $(CH_3)_3SiO$ and M' is $Si(CH_3)_3$

D is $(CH_3)_2SiO$ and D' is $(CH_3)(R)SiO$ where $R=(CH_2)_nO(C_2H_4O)_a(C_3H_6O)_bR_1$, $R_1$ is H, an alkyl group having 1 to 4 carbon atoms, an alkyl ester group wherein the alkyl group of the ester has 1 to 4 carbon atoms:

n is from 2 to 4;

a is from 3 to 25;

b is from 0 to 25;

wherein Y is from 0 to 5; and

X is from 1 to 5; and b) from 99 to 1% by weight of at second surfactant of the formula $$R_4O(CH_2CH_2O)_nR_5$$

where n is 1 to 50;

$R_4$ is an alkyl group or an aryl group optionally having an alkyl substituent with up to 20 carbon atoms;

$R_5$ is selected from hydrogen and alkyl groups having from 1 to 4 carbon atoms.

15. A method of treating turf or soil to alleviate drought stress and soil capping and to improve soil water conservation, which comprises applying directly to the turf or soil a composition consisting essentially of an aqueous solution of:

a) from 1 to 99% by weight of an organosilicone compound of the general formula $$MD_yD_x'M'$$

where M is $(CH_3)_3SiO$ and M' is $Si(CH_3)_3$

D is $(CH_3)_2SiO$ and D' is $(CH_2)(R)SiO$ where $R=(CH_2)_nO(C_2H_4O)_a(C_3H_6O)_bR_1$, $R_1$ is H, an alkyl group having 1 to 4 carbon atoms, an alkyl ester group wherein the alkyl group of the ester has 1 to 4 carbon atoms:

n is from 2 to 4;

a is from 3 to 25;

b is from 0 to 25;

wherein Y is from 0 to 5; and

X is from 1 to 5; and b) a second surfactant of the formula $$R_4O(CH_2CH_2O)_nR_5$$

where n is 1 to 50;

$R_4$ is an alkyl group or an aryl group optionally having an alkyl substituent with up to 20 carbon atoms;

$R_5$ is selected from hydrogen and alkyl groups having from 1 to 4 carbon atoms.

c) a polyalkylene oxide compound of general formula $$R_3-O-(C_2H_4O)c(C_3H_6O)_dR_3$$

where c is 0 to 300; d is 0 to 300, $R_3$ is selected from H and alkyl groups with 1 to carbon atoms; the polyalkylene oxide having a molecular weight of 300 to wherein the total amount by weight of (b) and (c) is from 99% to 1%.

16. A composition for treating turf or soil to alleviate drought stress and soil capping and to improve soil water conservation, which composition consists essentially of an aqueous solution of:

a) from 1 to 99% by weight of an organosilicone compound of the general formula $$MD_yD_x'M'$$

where M is $(CH_3)_3SiO$ and M' is $Si(CH_3)_3$

D is $(CH_3)_2SiO$ and D' is $(CH_3)(R)SiO$ where $R=(CH_2)_nO(C_2H_4O)_a(C_3H_6O)_bR_1$, $R_1$ is H, an alkyl group having 1 to 4 carbon atoms, an alkyl ester group wherein the alkyl group of the ester has 1 to 4 carbon atoms:

n is from 2 to 4;

a is from 3 to 25;

b is from 0 to 25;

wherein Y is from 0 to 5; and

X is from 1 to 5; and b) from 99 to 1% by weight of at second surfactant of the formula $$R_4O(CH_2CH_2O)_nR_5$$

where n is 1 to 50;

$R_4$ is an alkyl group or an aryl group optionally having an alkyl substituent with up to 20 carbon atoms;

$R_5$ is selected from hydrogen and alkyl groups having from 1 to 4 carbon atoms.

17. A composition for treating turf or soil to alleviate drought stress and soil capping and to improve soil water conservation, which composition consists essentially of an aqueous solution of:

a) from 1 to 99% by weight of an organosilicone compound of the general formula $$MD_yD_x'M'$$

where M is $(CH_3)_3SiO$ and M' is $Si(CH_3)_3$

D is $(CH_3)_2SiO$ and D' is $(CH_3)(R)SiO$ where $R=(CH_2)_nO(C_2H_4O)a(C_3H_6O)_bR_1$, $R_1$ is H, an alkyl group having 1 to 4 carbon atoms, an alkyl ester group wherein the alkyl group of the ester has 1 to 4 carbon atoms:

n is from 2 to 4;

a is from 3 to 25;

b is from 0 to 25;

wherein Y is from 0 to 5; and

X is from 1 to 5; and b) a second surfactant of the formula $$R_4O(CH_2CH_2O)_nR_5$$

where n is 1 to 50;

$R_4$ is an alkyl group or an aryl group optionally having an alkyl substituent with up to 20 carbon atoms;

$R_5$ is selected from hydrogen and alkyl groups having from 1 to 4 carbon atoms.

c) a polyalkylene oxide compound of general formula $$R_3\text{—}O\text{—}(C_2H_4O)c(C_3H_6O_d)R_3$$

where c is 0 to 300; d is 0 to 300, $R_3$ is selected from H and alkyl groups with 1 to 4 carbon atoms; the polyalkylene oxide having a molecular weight of 300 to 15000; wherein the total amount by weight of (b) and (c) is from 99% to 1%.

* * * * *